United States Patent
Warner et al.

(12)

(10) Patent No.: US 7,790,922 B2
(45) Date of Patent: Sep. 7, 2010

(54) PURIFICATION OF ACETIC ACID FROM WOOD ACETYLATION PROCESS USING EXTRACTION

(75) Inventors: R. Jay Warner, Houston, TX (US); Melchior A. Meilchen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 364 days.

(21) Appl. No.: 12/075,928

(22) Filed: Mar. 14, 2008

(65) Prior Publication Data
US 2009/0234157 A1 Sep. 17, 2009

(51) Int. Cl.
*C07C 51/42* (2006.01)
(52) U.S. Cl. ..................................................... 562/608
(58) Field of Classification Search ........................ None
See application file for complete search history.

(56) References Cited

U.S. PATENT DOCUMENTS 3,496,159 A   2/1970  Spence ...................... 260/97.6
5,525,721 A   6/1996  Ohshima et al. .............. 536/69
2004/0258941 A1  12/2004  Neogi et al. ............. 428/537.1

FOREIGN PATENT DOCUMENTS

| EP | 0 213 252 A1 | 3/1987 |
| EP | 0 680 810 A1 | 11/1995 |
| EP | 0 686 619 A1 | 12/1995 |
| WO | WO 2005/077626 A1 | 8/2005 |

*Primary Examiner*—Paul A Zucker
(74) *Attorney, Agent, or Firm*—Michael W. Ferrell

(57) ABSTRACT

There is shown a method of purifying glacial acetic acid containing terpene and terpenoid impurities. Substantially dry acetic acid containing terpene and terpenoid impurities is combined with water and a suitable organic solvent, which is substantially immiscible with acetic acid and water, to form a separating composite extraction medium having a weight ratio of acetic acid:water of at least 1:1. The components are separated into an organic phase and an aqueous acid phase, with the terpene and terpenoid impurities concentrated in the organic phase, and with the aqueous acid phase purified of terpene and terpenoid impurities. The purified aqueous acid phase is recovered, and the purified acetic acid is dried.

13 Claims, 3 Drawing Sheets

PURIFICATION OF ACETIC ACID FROM WOOD ACETYLATION PROCESS USING EXTRACTION

FIELD OF INVENTION

The present invention relates to purification of acetic acid recovered from a wood acetylation process, and in particular, to removal of terpene and terpenoid impurities from the acid.

BACKGROUND OF THE INVENTION

Acetylation of wood improves its resistance to degradation. Commercial processes include variants of the process disclosed in WO 2005/077626 A1 of New Zealand Forest Research Institute Limited. See, also, United States Publication No. 2004/0258941 to Neogi et al., EP 0213252 A1 of Rowell et al., U.S. Pat. No. 5,525,721 to Ohshima et al., and EP 0680810 A1 of Stichting Hout Research for similar and related disclosure.

Generally speaking, the wood acetylation process noted above includes the steps of contacting wood with acetic anhydride to acetylate the cellulose to provide rot and termite resistance. During this process, a byproduct stream including an acetic anhydride/acetic acid mixture is generated. The acetic anhydride is separated from the acid and recycled back to the acetylation step, while the spent acetic acid must be purified before it is used in other products and/or reprocessed into acetic anhydride by way of ketene reaction, for example. If the spent acetic acid is not purified, final product quality will be impacted.

Recovery and separation of an acetic anhydride/acetic acid mixture after completion of a wood acetylation step is known in the art. In EP 0213252 A1 and EP 0680810 A1 (discussed above) it is noted that the acid can be purified by way of fractional distillation. Acid purification by distillation is also disclosed in U.S. 2004/0258941 (discussed above), and JP 56008016 B of Daicel Chemical Industries, Ltd. See, also, U.S. Pat. No. 3,496,159 to Spence for fractional distillation of acids generally.

In EP 686619 of Commissariat a L'Energie Atomique, it is noted that organic impurities can be removed from condensed acetic acid vapor recovered from a distillation column by way of extraction.

While the foregoing methods are no doubt effective to somewhat purify the recovered acetic acid, it has been found that terpenes and terpenoid impurities, especially high boiling-point compounds, are difficult to remove and present a challenging technical obstacle to reuse of the recovered acetic acid in applications requiring high purity product. The problem is particularly difficult with "dry" acetic acid since terpene and terpenoid impurities are soluble in concentrated or glacial acetic acid.

SUMMARY OF THE INVENTION

In order to address the difficulties mentioned above, a method of purifying acetic acid containing terpene and terpenoid impurities is provided. The method includes generally combining acetic acid containing terpene and terpenoid impurities, water and a suitable organic solvent, which is substantially immiscible with acetic acid together with water, to form a separating composite extraction medium. In most cases, the weight ratio of acetic acid:water is at least 1:1. The components are then separated into an organic phase and an aqueous acid phase, wherein the terpene and terpenoid impurities are concentrated in the organic phase, and the aqueous acid phase is purified of terpene and terpenoid impurities. The purified aqueous acid phase is recovered and dried.

Other aspects and advantages of the present invention are described in the detailed description below.

BRIEF DESCRIPTION OF THE DRAWINGS

The invention is described in detail below with reference to the appended drawings, wherein like numerals designate similar parts. In the Figures.

DETAILED DESCRIPTION OF THE INVENTION

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below. Percentages, ppm, and so forth are on a weight basis unless otherwise specified.

The term "glacial acetic acid" as used herein refers to acetic acid that contains less than 0.2 weight % water.

The term "organic impurities" as used herein refers to a variety of impurities contained in acetic acid recovered from the acetylation process. Such impurities may include terpinenes, terpinolenes, α-terpineol acetate, α-terpineol, α-pinene, α-fenchene, camphene, p-methyl isopropyl benzene (p-cymene), limonenes, α-fenchyl acetate, isobornyl acetate, pinocarvyl acetate, acetaldehyde, acetone, acetonitrile, methyl acetate, ethyl acetate, methoxy acetic acid, and propionic acid.

The term "light-ends" as used herein refers to a number of impurities present in recovered acetic acid that have boiling points lower than that of acetic acid. These compounds include those identified below along with their chemical structures.

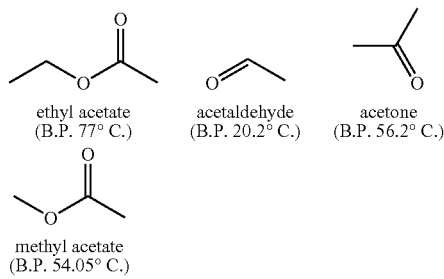

ethyl acetate (B.P. 77° C.)   acetaldehyde (B.P. 20.2° C.)   acetone (B.P. 56.2° C.)

methyl acetate (B.P. 54.05° C.)

The term "terpene and terpenoid impurities" as used herein refers to impurities found in recovered acetic acid used in the process disclosed in WO 2005/077626 A1. Terpenes are derivatives of isoprene, + can be acyclic, monocyclic, or bicyclic, and are generally unsaturated. Terpenoids are saturated isomers and derivatives of terpenes, such as alcohols, aldehydes, and esters. These impurities include the compounds identified below, along with their chemical structures.

Note that different isomers are sometimes simply referred to by their generic names herein. Note also reference to one genus or class of compounds in plural form contemplates reference to isomers or members within the genus or class.

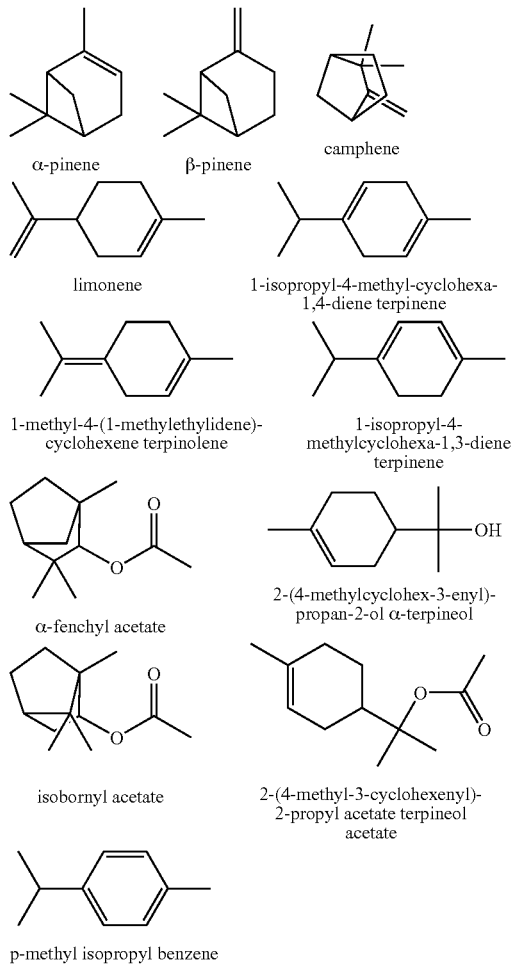

Figure 1:
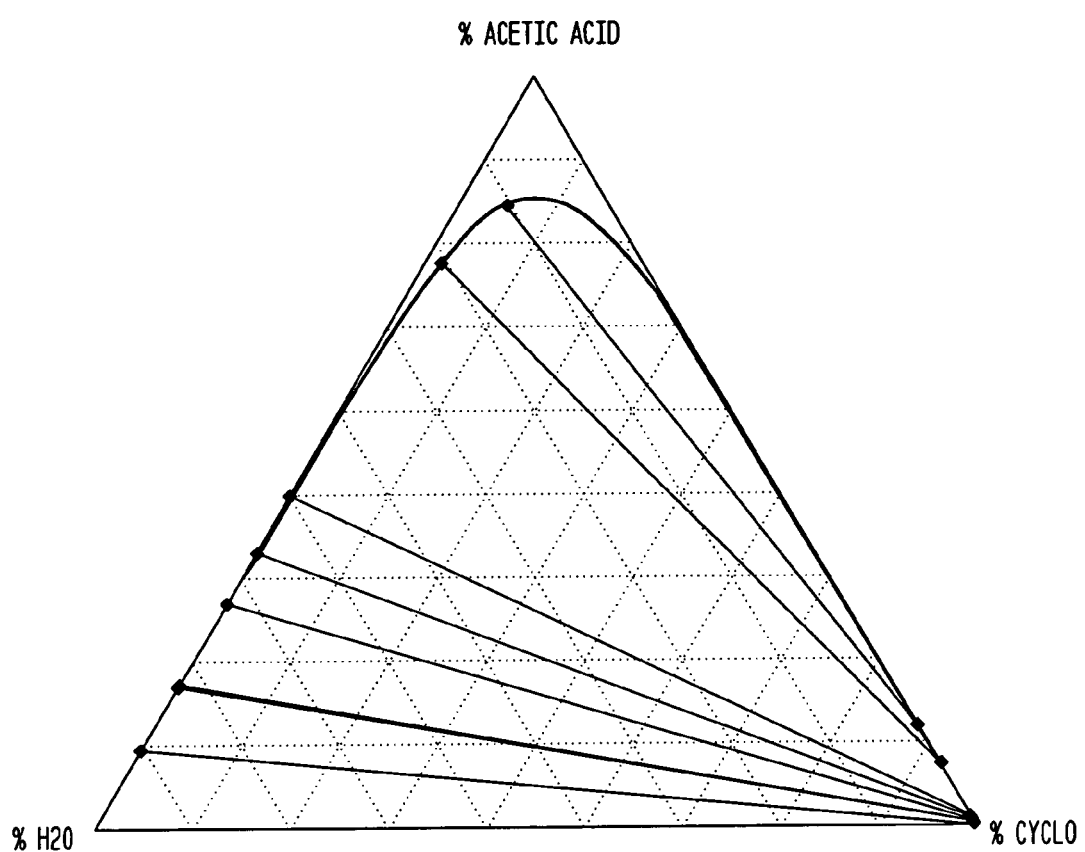
FIG. 1 is a liquid-liquid extraction ternary diagram for a cyclohexane-acetic acid-water system.

The terpene and terpenoid impurities found in acetic acid recovered from a wood acetylation process are essentially insoluble in water and in weak aqueous acetic acid mixtures. However, the terpene/terpenoid impurities are soluble in concentrated acetic acid and in certain solvents, such as cyclohexane and other hydrocarbons. At sufficiently low concentrations of acetic acid, mixtures of recovered acetic acid, water, and solvent separate into an organic phase comprising primarily the solvent and impurities, and an aqueous phase comprising primarily acetic acid and water. For example, the liquid-liquid equilibrium phase diagram for a cyclohexane/acetic acid/water mixture of FIG. 1 shows the two-phase region (under the curve) and the single-phase region (above the curve). Tie-lines included in the diagram indicate the composition of the two phases formed from initial mixture compositions along the tie-line. The compositions of the phases are represented by the intersection of the tie line with the phase curve.

Figure 2:
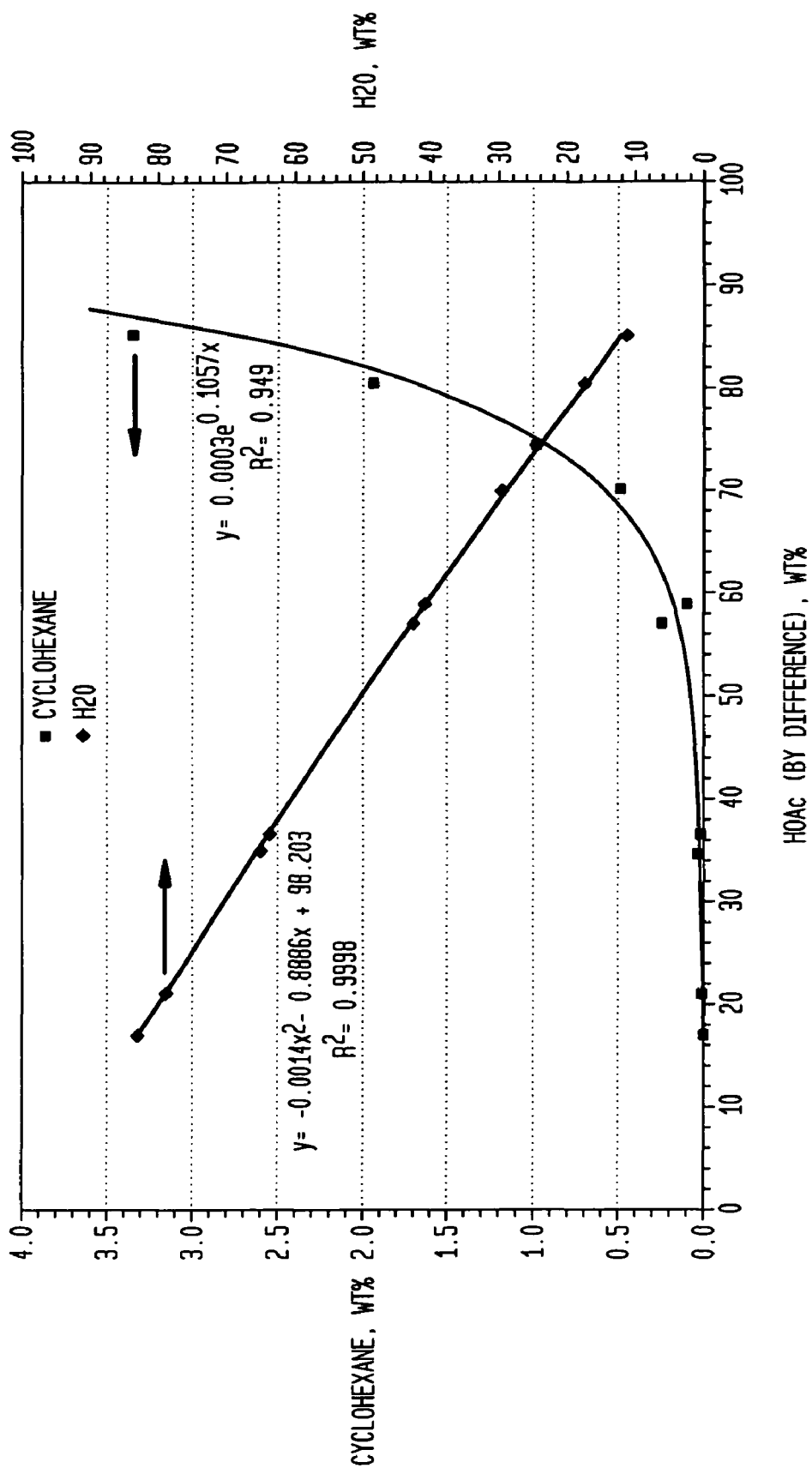
FIG. 2 is a diagram of liquid-liquid extraction data showing aqueous phase acetic acid vs. cyclohexane and water concentration.

FIG. 2 provides the general relationship between aqueous acetic acid concentrations and the corresponding levels of cyclohexane dissolved in the aqueous phase. As FIG. 2 shows, essentially no cyclohexane is present in the aqueous phase up to acetic acid concentrations of approximately 35 weight %. As the acetic acid concentration increases, the amount of cyclohexane present in the aqueous phase increases. Once the acetic acid concentration reaches approximately 90 weight %, the separating composite extraction medium no longer separates into an aqueous and an organic phase.

The organic phase solvent used in connection with the process of this invention may be an aromatic or aliphatic hydrocarbon, or may have an ester, ether, ketone, amine, nitrated or chlorinated functional group. Preferably, the solvent is an aliphatic or aromatic hydrocarbon with 6 to 10 carbons. For example, the solvent may be benzene, toluene, turpentine oil, cyclohexane, cyclohexene, cycloalkane, cyclopropane, cyclopentane, cyclopentadiene, cyclooctatetraene, dioxane, acetonitrile, chlorobenzene, heptane, hexane, diethyl ether, petroleum ether, mineral oil, fatty acid esters, or caprylate triglyceride. Generally suitable organic solvents are those that will extract terpene and terpenoid impurities as well as phase with an acetic acid-water mixture.

We have found that the partition coefficient, K, a ratio of the molar concentration of terpenoid impurities in the organic phase to the molar concentration of impurities in the aqueous phase is very high when using cyclohexane, and presumably when using other hydrocarbons, as the extraction solvent. See equation 1, below.

$$K = \frac{[\text{terpenoids}]_{organic}}{[\text{terpenoids}]_{aqueous}} \quad \text{Eq. (1)}$$

The amount of terpenoid impurities (gmoles) remaining in the aqueous acetic acid phase, x, after extracting with a solvent, like cyclohexane, can be estimated by knowledge of the partition coefficient, K, the initial amount of terpenoid impurities (gmoles), and the amount of aqueous and solvent (organic) solutions using the following equation 2.

$$x = V_{aq}/(V_{org}K + V_{aq})a, \text{ where} \quad \text{Eq. (2)}$$

a=initial gmoles
x=remaining gmoles
$V_{org}$=amount of solvent (e.g., kg)
$V_{aq}$=amount of aqueous acetic acid (e.g., kg)

A typical molecular weight for monoterpenoids, $C_{10}H_{16}$, is 136.23.

EXAMPLES 1 and 2

Two initial mixtures of cyclohexane, water, and acetic acid spiked with several terpenes/terpenoids were mixed well and allowed to phase into cyclohexane (top) and aqueous acetic acid (lower) layers, which were then individually analyzed. Table 1 below summarizes the initial terpene and terpenoid impurity concentrations in the acetic acid before extraction, and the impurity concentrations in the aqueous and organic phases after extraction for two ratios of acetic acid to solvent and water. As noted, AAwT represents acetic acid containing terpene and terpenoid impurities.

TABLE 1

Results of Examples 1 and 2
Terpene/Terpenoid Concentrations, ppm

| Ratio (w/w) | Sample | Pinene | Camphene | p-Cymene | Limonene | Terpinene | Terpinolene | α-Terpineol acetate | Total Terpenoids | Terpenoids, Molality |
|---|---|---|---|---|---|---|---|---|---|---|
| 100 | Acetic Acid with Terpenoids | 40.3 | 32.9 | 19.7 | 143.7 | 6.2 | 32.7 | 3.8 | 279.3 | 0.00205 |
| 20:30:50 | Cyclohexane/ AAwT/H2O | | | | | | | | | |
| | aqueous | ND | ND | ND | ND | ND | ND | ND | ~0 | 0.00000 |
| | organic | 61.5 | 50.9 | 28.8 | 214.7 | 9.4 | 48.8 | 6.2 | 420 | 0.00308 |
| 10:60:30 | Cyclohexane/ AAwT/H2O | | | | | | | | | |
| | aqueous | ND | ND | ND | 2.9 | ND | ND | ND | ~2.9 | 0.00002 |
| | organic | 250.4 | 198.9 | 112.4 | 862.3 | 38.6 | 193.6 | 19.9 | 1676 | 0.01230 |

HOAc with Terpenoids = AAwT
ND = non-detectable
Molality = gmole/kg
Terpenoids M.W. ~136.23

The partition coefficient calculated for the 10:60:30 cyclohexane/acetic acid/water experimental results (Table 1), which corresponded to an aqueous acetic acid concentration of ~66.7 wt %, was K=[0.01230]/[0.00002]=578.

EXAMPLES 3 to 12

A more extensive set of tests were performed to determine terpene/terpenoid extraction coefficients for this system at different initial concentrations of substantially anhydrous acetic acid, water, and cyclohexane. The compositions listed in Table 2 were used to prepare the ten tests. The reagents were well mixed at room temperature. Two phases were formed and separated, and an analysis was performed.

TABLE 2

Cyclohexane/Acetic Acid/Water Liquid/Liquid Extraction Experiment Compositions
LLE Experimental Mixtures, wt %

| | ID # | | | | | | | | | |
|---|---|---|---|---|---|---|---|---|---|---|
| | 1 | 2 | 3 | 4 | 5 | 6 | 7 | 8 | 9 | 10 |
| Acetic Acid* | 10 | 20 | 30 | 40 | 50 | 60 | 70 | 70 | 15 | 30 |
| H2O | 45 | 40 | 35 | 30 | 25 | 20 | 15 | 10 | 70 | 62 |
| Cyclohexane | 45 | 40 | 35 | 30 | 25 | 20 | 15 | 20 | 15 | 8 |

*with terpenoids

The results of these extraction tests are presented in Table 3. The average acetic acid concentration for experiments 4, 5, and 6 was ~67 wt %. Similar two-stage runs were made and showed substantially complete removal, i.e., less than 0.03 ppm of the terpene and terpenoid impurities mentioned above.

TABLE 3

Summary of Analytical Results for LLE Experiments: Acetic Acid with Terpenoids/Water/Cyclohexane

| Sample ID # | Terpenoid Components, ppm | | | | | | | | | | Cyclohexane wt % | HOAc wt % | H2O wt % |
|---|---|---|---|---|---|---|---|---|---|---|---|---|---|
| | Pinene | Camphene | p-Cymene | Limonene | Terpinene | Terpinolene | α-Fenchyl Acetate | Bornyl Acetate | α-Terpineol Acetate | Total Terpenes | | | |
| Acetic Acid* Organic Layer | 14.5 | 20.6 | 19.9 | 144 | 5.8 | 28.2 | 0.2 | 0.6 | 0.4 | 234 | | | |
| #1 top | 3.9 | 5.3 | 5.6 | 39.7 | 1.6 | 8.0 | | | 1.4 | 66 | 99.62 | 0.22 | 0.15 |
| #2 top | 15.6 | 22.1 | 22.3 | 156.5 | 6.2 | 31.7 | | 0.7 | | 255 | 99.29 | 0.67 | 0.02 |
| #3 top | 9.9 | 13.6 | 14.3 | 100.5 | 4.0 | 20.4 | | 0.5 | | 163 | 98.65 | 1.26 | 0.07 |
| #4 top | 25.3 | 36.1 | 35.7 | 252.1 | 10.2 | 50.7 | | 1.4 | | 412 | 97.93 | 1.99 | 0.04 |
| #5 top | 40.9 | 57.8 | 57.1 | 405.3 | 16.4 | 81.0 | | 2.0 | | 661 | 97.24 | 2.61 | 0.09 |
| #6 top | 120.7 | 173.3 | 168.2 | 1201.1 | 48.9 | 235.8 | 0.8 | 5.3 | | 1954 | 95.67 | 4.10 | 0.04 |
| #7 top | 99.5 | 137.1 | 124.6 | 947.8 | 38.3 | 180.5 | 0.6 | 3.0 | | 1531 | 93.37 | 6.47 | 0.01 |
| #8 top | 79.1 | 112.5 | 104.5 | 783.7 | 31.5 | 147.4 | | 0.9 | | 1260 | 90.36 | 9.28 | 0.24 |

TABLE 3-continued

Summary of Analytical Results for LLE Experiments: Acetic Acid with Terpenoids/Water/Cyclohexane

| Sample ID # | Terpenoid Components, ppm | | | | | | | | | | Cyclo-hexane wt % | HOAc wt % | H2O wt % |
|---|---|---|---|---|---|---|---|---|---|---|---|---|---|
| | Pinene | Camphene | p-Cymene | Limonene | Terpinene | Terpinolene | α-Fenchyl Acetate | Bornyl Acetate | α-Terpineol Acetate | Total Terpenes | | | |
| #9 top | 18.2 | 26.1 | 26.5 | 185.8 | 7.4 | 37.7 | | 0.7 | | 302 | 99.63 | 0.19 | 0.15 |
| #10 top | 68.5 | 99.6 | 100.3 | 693.5 | 27.9 | 139.6 | | 3.7 | | 1133 | 99.22 | 0.65 | 0.01 |
| Aqueous Layer | | | | | | | | | | | | | |
| #1 btm | | | | | | | | | | | 0.01 | 21.16 | 78.83 |
| #2 btm | | | | | | | | | | | 0.03 | 34.95 | 65.02 |
| #3 btm | | | | | | | | | | | 0.09 | 59.04 | 40.87 |
| #4 btm | | | | 0.82 | | 0.51 | | | | 1.3 | 0.24 | 57.12 | 42.64 |
| #5 btm | | | | 0.77 | | 0.53 | | | | 1.3 | 0.48 | 70.14 | 29.38 |
| #6 btm | | | 0.59 | 1.69 | | | | | | 2.3 | 0.99 | 74.49 | 24.52 |
| #7 btm | 1.01 | 1.28 | 2.14 | 8.29 | | 2.60 | | | 1.19 | 16.5 | 1.93 | 80.50 | 17.57 |
| #8 btm | 1.28 | 1.80 | 2.68 | 11.2 | | 3.25 | | | 1.35 | 21.5 | 3.35 | 85.10 | 11.55 |
| #9 btm | | | | | | | | | | | 0.00 | 17.12 | 82.88 |
| #10 btm | | | | | | | | | | | 0.00 | 36.59 | 63.41 |

*with terpenoids

We have found that the partition coefficient, K, for terpenoid impurities in the cyclohexane/acetic acid/water system varies with the concentration of acetic acid in the aqueous phase. The partition coefficient, K, was found to be indirectly proportional to the acetic acid concentration. The partition coefficient, based on the data presented in Table 3, was calculated to be in a range of about 560+/−290 corresponding to an aqueous acetic acid concentration of about 66+/−11 wt %.

It is apparent from the foregoing that the partition coefficient is so large that only one or two extraction stages using cyclohexane are necessary to remove essentially all terpene/terpenoid impurities from an aqueous acetic acid solution.

The energy consumption for the combined extraction/distillation process is primarily dependent upon the amount of water used in the extraction step. Acetic acid losses account for the other major variable operating cost. Therefore, these factors are considered in determining the appropriate mixture ratios.

Figure 3:
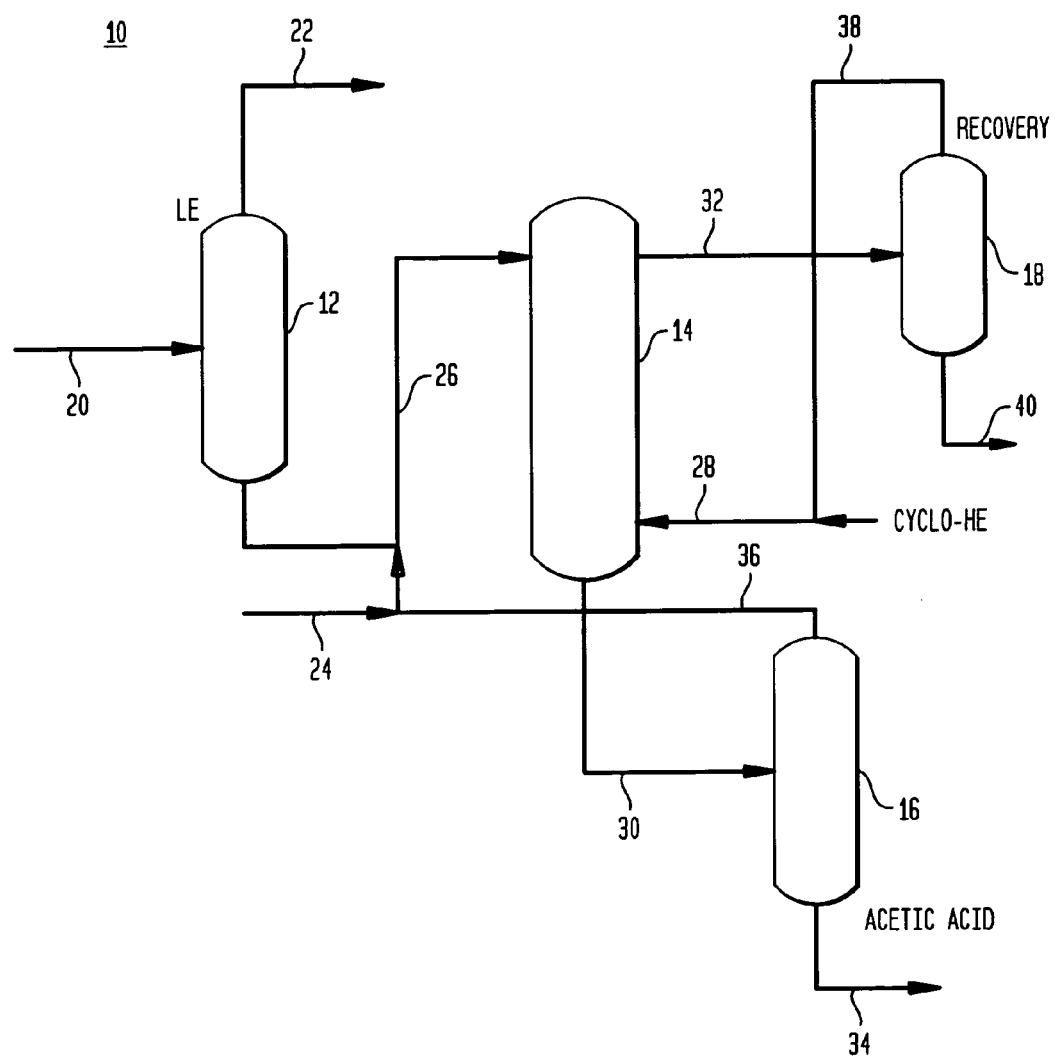
FIG. 3 is a schematic diagram illustrating an extraction system for purifying acetic acid.

A suitable apparatus for practicing the invention continuously is shown in FIG. 3. Apparatus 10 for purifying acetic acid consists of a light-ends stripper 12, and extraction tower 14, a drying tower 16, and a solvent stripper 18.

The substantially anhydrous acetic acid to be purified (optionally including acetic anhydride) is fed via feed line 20 to the light-ends stripper 12. Light-end compounds, such as acetone, methyl acetate, and acetaldehyde, etc. are removed at the overhead line 22. The remainder is discharged from the light-ends stripper, combined with water via line 24, and fed to the extraction tower 14 via line 26. Solvent is fed to the extraction tower 14 via line 28.

Extraction tower 14 may be of any suitable type known in the art, such as a mixer-settler, tray or packed extraction tower, perforated-plate tower, baffle tower, agitated tower extractor, pulse column, or centrifugal extractor. In the extraction tower 14, the components mix and separate into an aqueous acid phase and an organic phase. Purified aqueous acetic acid, i.e. the aqueous acid phase, is discharged from the extraction tower 14 and fed to the drying tower 16 via line 30 to separate water from the acid. The organic phase comprising a solvent and terpene and terpenoid impurities is drawn off the top of the extraction tower 14 and fed to the solvent stripper 18 via line 32.

The dried, purified acetic acid is removed from the drying tower via line 34, and water, containing some residual acetic acid, is returned via line 36 to extraction tower feed line 26. Solvent recovered from the solvent stripper 18 is returned to the extraction tower via line 38. Recovered solvent contains small amounts of acetic acid and water. Impurities are discharged from the solvent stripper 18 as heavy ends through line 40.

There is thus provided a method of purifying acetic acid containing terpene and terpenoid impurities including: (a) combining acetic acid containing terpene and terpenoid impurities, water and a suitable organic solvent which is substantially immiscible with acetic acid and water to form a separating composite extraction medium wherein the weight ratio of acetic acid:water is at least 1:1; (b) separating the components of step (a) into an organic phase and an aqueous acid phase, wherein the terpene and terpenoid impurities are concentrated in the organic phase and the aqueous acid phase is purified of terpene and terpenoid impurities; (c) recovering the purified aqueous acid phase; and (d) drying the purified acetic acid.

In one preferred embodiment, acetic acid containing terpene and terpenoid impurities is recovered from a wood acetylation process. The method typically provides removal of 70% or more of the terpene and terpenoid impurities from the acetic acid on a weight basis and more preferably removes 80% or 90% or more of the terpene and terpenoid impurities from the acetic acid on a weight basis.

In many cases, acetic acid supplied to the separating composite extraction medium contains more than 200 ppm terpene and terpenoid impurities, based on the combined weight of acid and impurities, and the purified acid contains less than 50 ppm terpene and terpenoid impurities, based on the weight of acid and impurities; more typically, acetic acid supplied to the separating composite extraction medium contains more than 200 ppm terpene and terpenoid impurities, based on the combined weight of acid and impurities, and the purified acid contains less than 40 or 30 ppm terpene and terpenoid impurities, based on the weight of acid and impurities only. Still more preferably, acetic acid supplied to the separating composite extraction medium contains more than 200 ppm terpene and terpenoid impurities, based on the combined weight of acid and impurities, and the purified acid contains less than 20 ppm terpene and terpenoid impurities, based on the weight of acid and impurities.

It is likewise preferred to use less water than acetic acid in the extraction process, for example wherein weight ratio of acetic acid:water in the separating composite extraction medium is greater than 1.25:1; greater than 1.5:1; or greater than 1.75:1, such as greater than 2:1. In most cases the weight ratio of acetic acid:water in the separating composite extraction medium is greater than 2:1 and less than 7:1.

A weight ratio of acetic acid:solvent in the separating composite extraction medium is suitably at least 0.2:1 and up to the maximum ratio where the system will phase, about 10:1 or so. See FIG. 1. In preferred case, the weight ratio of acetic acid:solvent in the separating composite extraction medium is at least 1:1; at least 1.5:1; at least 2:1; or at least 3:1.

A preferred organic solvent is cylohexane.

The method optionally includes stripping light-end compounds from the acetic acid containing terpene and terpenoid impurities before combining the acetic acid containing terpene and terpenoid impurities, water, and solvent. Likewise, the method may further include: (a) recovering the organic phase; (b) feeding the organic phase to a solvent stripper column; and (c) separating the solvent from terpene and terpenoid impurities in the solvent stripper column.

In another aspect of the invention, there is provided a method of purifying glacial acetic acid containing terpene and terpenoid impurities including: (a) combining substantially dry acetic acid containing terpene and terpenoid impurities, water and a suitable organic solvent which is substantially immiscible with acetic acid and water to form a separating composite extraction medium wherein the weight ratio of acetic acid:water is at least 1:1; (b) separating the components of step (a) into an organic phase and an aqueous acid phase, wherein the terpene and terpenoid impurities are concentrated in the organic phase and the aqueous acid phase is purified of terpene and terpenoid impurities; (c) recovering the purified aqueous acid phase; and (d) drying the purified acetic acid.

Still another aspect of the invention is a method of purifying acetic acid recovered from a wood acetylation process containing terpene and terpenoid impurities including: (a) combining acetic acid containing terpene and terpenoid impurities, water and a suitable organic solvent which is substantially immiscible with acetic acid and water to form a separating composite extraction medium; (b) separating the components of step (a) into an organic phase and an aqueous acid phase, wherein the terpene and terpenoid impurities are concentrated in the organic phase and the aqueous acid phase is purified of terpene and terpenoid impurities; (c) recovering the purified aqueous acid phase; and (d) drying the purified acetic acid, wherein the terpene and terpenoid impurities comprise impurities selected from the group consisting of: terpinenes; terpinolenes; α-terpineol acetate; pinenes; α-fenchene; camphene; p-methyl isopropyl benzene (p-cymene); limonenes; α-fenchyl acetate; isobornyl acetate; and mixtures thereof. Typically the method provides removal of 70% or more of the terpinenes present in the acid before purification; removal of 70% or more of the terpinolenes present in the acid before purification; removal of 70% or more of the α-terpineol acetate present in the acid before purification; removal of 70% or more of the pinenes present in the acid before purification; removal of 70% or more of the α-fenchene present in the acid before purification; removal of 70% or more of camphene present in the acid before purification; removal of 70% or more of p-methyl isopropyl benzene (p-cymene) present in the acid before purification; removal of 70% or more of limonenes present in the acid before purification; removal of 70% or more of α-fenchyl acetate present in the acid before purification; as well as 70% or more of isobornyl acetate present in the acid before purification. 80% or 90% removal of each of these impurities is readily achieved.

The purified and dried acid contains less than 5 ppm of the following compounds: terpinenes; terpinolenes; α-terpineol acetate; pinenes; α-fenchene; camphene; p-methyl isopropyl benzene (p-cymene); limonenes; α-fenchyl acetate; and isobornyl acetate.

While the invention has been described in connection with purifying acetic acid in connection with particular Examples, modifications within the spirit and scope of the present invention, set forth in the appended claims, will be readily apparent to those of skill in the art.

What is claimed is:

1. A method of purifying glacial acetic acid containing terpene and terpenoid impurities, comprising:
 (a) combining substantially dry acetic acid containing terpene and terpenoid impurities, water and a suitable organic solvent, which is substantially immiscible with acetic acid and water, to form a separating composite extraction medium wherein the weight ratio of acetic acid:water is at least 1:1;
 (b) separating the components of step (a) into an organic phase and an aqueous acid phase, wherein the terpene and terpenoid impurities are concentrated in the organic phase and the aqueous acid phase is purified of terpene and terpenoid impurities;
 (c) recovering the purified aqueous acid phase; and
 (d) drying the purified acetic acid.

2. A method of purifying acetic acid recovered from a wood acetylation process containing terpene and terpenoid impurities, comprising:
 (a) combining substantially dry acetic acid containing terpene and terpenoid impurities, water and a suitable organic solvent, which is substantially immiscible with acetic acid and water, to form a separating composite extraction medium;
 (b) separating the components of step (a) into an organic phase and an aqueous acid phase, wherein the terpene and terpenoid impurities are concentrated in the organic phase and the aqueous acid phase is purified of terpene and terpenoid impurities;
 (c) recovering the purified aqueous acid phase; and
 (d) drying the purified acetic acid;
wherein the terpene and terpenoid impurities comprise impurities selected from the group consisting of: terpinenes; terpinolenes; α-terpineol acetate; pinenes; α-fenchene; camphene; p-methyl isopropyl benzene (p-cymene); limonenes; α-fenchyl acetate; isobornyl acetate; and mixtures thereof.

3. The method of purifying acetic acid according to claim 2, wherein the method provides removal of 70% or more of the terpinenes present in the acid before purification.

4. The method of purifying acetic acid according to claim 2, wherein the method provides removal of 70% or more of the terpinolenes present in the acid before purification.

5. The method of purifying acetic acid according to claim 2, wherein the method provides removal of 70% or more of the α-terpineol acetate present in the acid before purification.

6. The method of purifying acetic acid according to claim 2, wherein the method provides removal of 70% or more of the pinenes present in the acid before purification.

7. The method of purifying acetic acid according to claim 2, wherein the method provides removal of 70% or more of the α-fenchene present in the acid before purification.

8. The method of purifying acetic acid according to claim 2, wherein the method provides removal of 70% or more of camphene present in the acid before purification.

9. The method of purifying acetic acid according to claim 2, wherein the method provides removal of 70% or more of p-methyl isopropyl benzene (p-cymene) present in the acid before purification.

10. The method of purifying acetic acid according to claim 2, wherein the method provides removal of 70% or more of the limonenes present in the acid before purification.

11. The method of purifying acetic acid according to claim 2, wherein the method provides removal of 70% or more of the α-fenchyl acetate present in the acid before purification.

12. The method of purifying acetic acid according to claim 2, wherein the method provides removal of 70% or more of isobornyl acetate present in the acid before purification.

13. The method of purifying acetic acid according to claim 2, wherein the purified and dried acid contains less than 5 ppm of the following compounds: terpinenes; terpinolenes; α-terpineol acetate; pinenes; α-fenchene; camphene; p-methyl isopropyl benzene (p-cymene); limonenes; α-fenchyl acetate; and isobornyl acetate.

* * * * *